United States Patent
Goble et al.

(10) Patent No.: US 8,002,769 B2
(45) Date of Patent: *Aug. 23, 2011

(54) ELECTROSURGICAL GENERATOR AND SYSTEM

(75) Inventors: Colin C. O. Goble, South Oxfordshire (GB); Anthony Keith Atwell, Newport (GB)

(73) Assignee: Gyrus Medical Limited, Cardiff (GB)

( * ) Notice: Subject to any disclaimer, the term of this patent is extended or adjusted under 35 U.S.C. 154(b) by 1050 days.

This patent is subject to a terminal disclaimer.

(21) Appl. No.: 11/890,527

(22) Filed: Aug. 7, 2007

(65) Prior Publication Data

US 2008/0009850 A1    Jan. 10, 2008

Related U.S. Application Data

(60) Continuation-in-part of application No. 11/260,189, filed on Oct. 28, 2005, now Pat. No. 7,491,199, which is a division of application No. 10/378,676, filed on Mar. 5, 2003, now Pat. No. 6,966,907, which is a continuation-in-part of application No. 10/228,284, filed on Aug. 27, 2002, now Pat. No. 6,984,231.

(60) Provisional application No. 60/314,650, filed on Aug. 27, 2001.

(30) Foreign Application Priority Data

May 27, 2002 (GB) .................................. 0212162.2

(51) Int. Cl.
    *A61B 18/14*    (2006.01)
(52) U.S. Cl. ............... 606/37; 606/42; 606/48; 606/51
(58) Field of Classification Search ............... 606/34–41, 606/45–52
See application file for complete search history.

(56) References Cited

U.S. PATENT DOCUMENTS 3,898,991 A    8/1975    Ikuno et al.
(Continued)

FOREIGN PATENT DOCUMENTS

DE    199 43 792 A1    2/2001
(Continued)

OTHER PUBLICATIONS

Japanese Office Action dated Oct. 20, 2009 in related Japanese Patent Application No. 2006-505914 and English Translation thereof.

(Continued)

*Primary Examiner* — Lee Cohen
(74) *Attorney, Agent, or Firm* — Nixon & Vanderhye P.C.

(57) ABSTRACT

An electrosurgical system includes a generator for generating radio frequency power, and an electrosurgical instrument including at least three electrodes. The generator includes a radio frequency output stage having at least a pair of RF output lines, and a power supply coupled to the output stage for supplying power to the output stage. A controller is operable to limit the radio frequency output voltage developed across the output lines to at least a first predetermined threshold value to produce a cutting RF waveform, and a second threshold value to produce a coagulating RF waveform. In a combined mode, the controller delivers both cutting and coagulating waveforms by alternating discontinuously between the first and second threshold values to form a blended signal. The system also includes means for feeding the waveform to the three or more electrodes such that the cutting RF waveform is delivered between a first pair of the electrodes, and the coagulating waveform is delivered between a second pair of the electrodes.

25 Claims, 10 Drawing Sheets

U.S. PATENT DOCUMENTS

| | | |
|---|---|---|
| 4,116,198 A | 9/1978 | Roos |
| 5,160,334 A | 11/1992 | Billings et al. |
| 5,976,132 A | 11/1999 | Morris |
| 6,113,596 A | 9/2000 | Hooven et al. |
| 6,174,309 B1 | 1/2001 | Wrublewski et al. |
| 6,203,542 B1 | 3/2001 | Ellsberry et al. |
| 6,416,509 B1 | 7/2002 | Goble et al. |
| 6,679,882 B1 | 1/2004 | Kornerup |
| 6,966,907 B2 * | 11/2005 | Goble .............................. 606/37 |
| 2003/0073990 A1 | 4/2003 | Goble et al. |
| 2004/0006340 A1 | 1/2004 | Latterell et al. |

FOREIGN PATENT DOCUMENTS

| | | |
|---|---|---|
| EP | 0754 437 A2 | 1/1997 |
| EP | 1 287 788 A1 | 3/2003 |
| JP | 06-30949 | 2/1994 |
| JP | 09-10223 | 1/1997 |
| JP | 2000-135222 | 5/2000 |
| JP | 2002-325772 | 11/2000 |
| JP | 2003-500099 | 1/2003 |
| WO | WO 96/37156 A1 | 11/1996 |
| WO | WO 98/38932 A1 | 8/1998 |
| WO | WO 00/53112 | 9/2000 |
| WO | WO 00/71043 A1 | 11/2000 |
| WO | WO 02/03874 A1 | 1/2002 |

OTHER PUBLICATIONS

Office Action, mailed May 30, 2008, in U.S. Appl. No. 11/260,189, filed Oct. 28, 2005.

International Search Report in International Application No. PCT/GB2004/000917, Oct. 6, 2004.

Official Partial International Search Report in International Application No. PCT/GB2004/000917 (3 pages).

Search Report in UK Application No. GB 0305018.4, Jun. 19, 2003.

Office Action mailed Feb. 18, 2011, in related U.S. Appl. No. 11/882,887, filed Aug. 6, 2007.

* cited by examiner

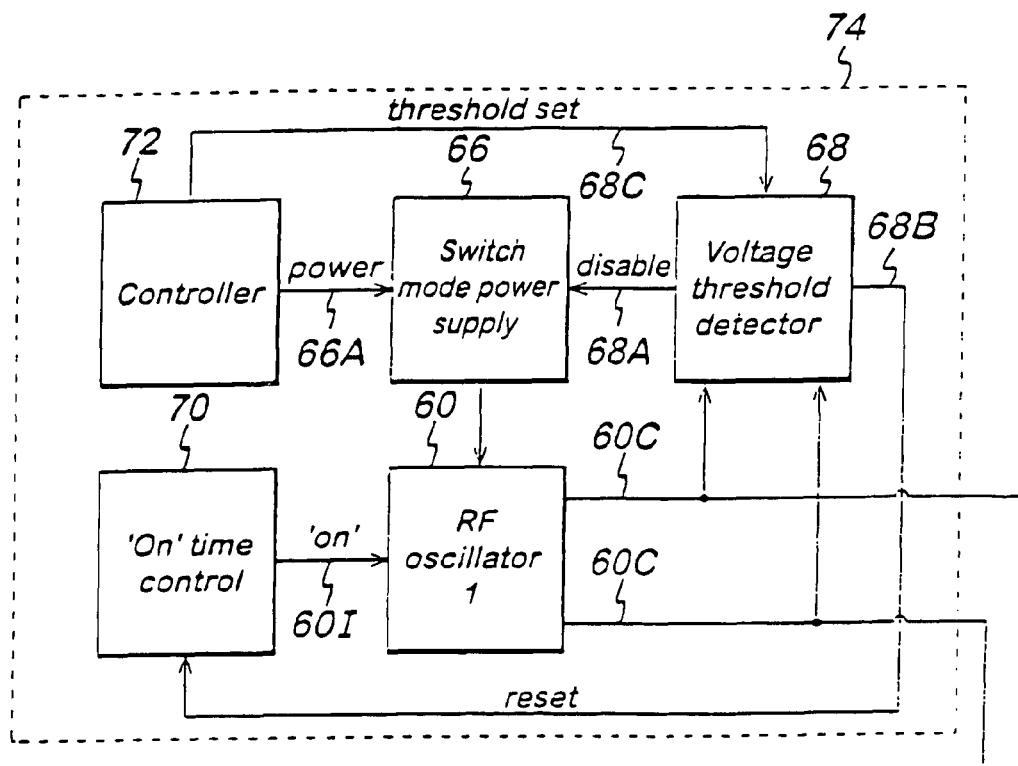
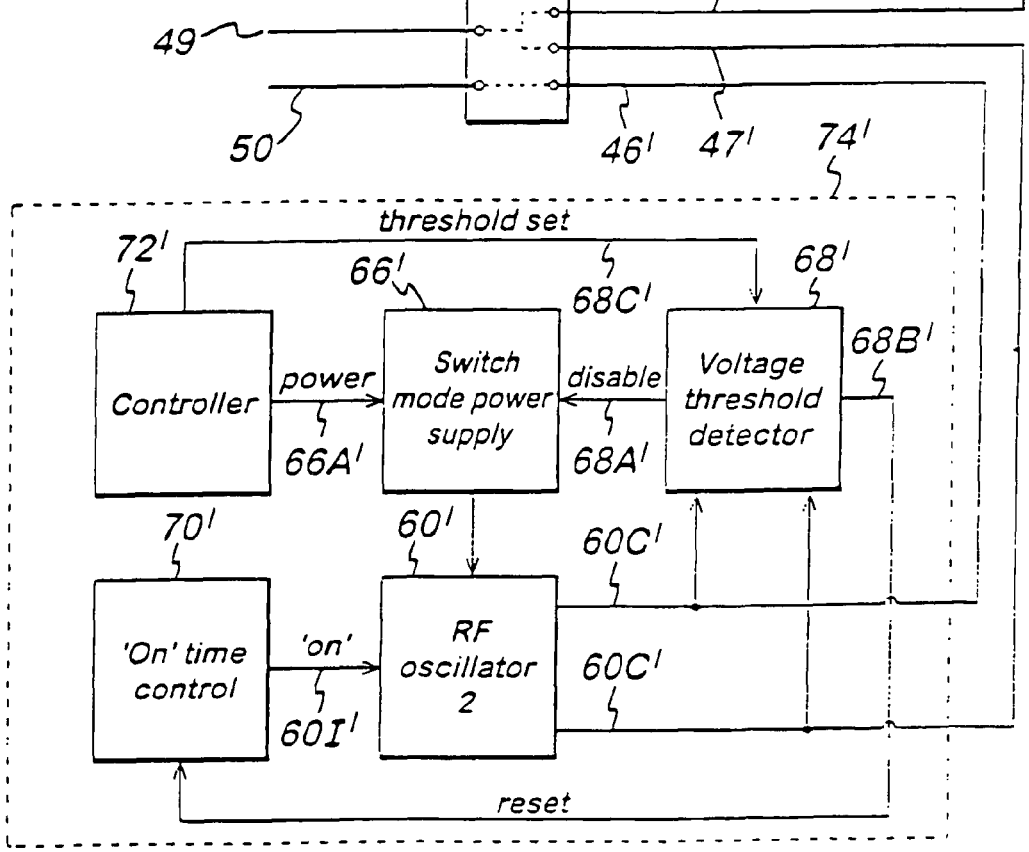
Fig. 9

ELECTROSURGICAL GENERATOR AND SYSTEM

CROSS REFERENCE TO RELATED APPLICATIONS

This is a continuation-in-part of U.S. application Ser. No. 11/260,189 filed Oct. 28, 2005, now U.S. Pat. No. 7,491,199, issued Feb. 17, 2009, which is a divisional of U.S. application Ser. No. 10/378,676 filed Mar. 5, 2003, now U.S. Pat. No. 6,966,907, issued Nov. 22, 2005, which is a continuation-in-part of U.S. application Ser. No. 10/228,284 filed Aug. 27, 2002, now U.S. Pat. No. 6,984,231, issued Jan. 10, 2006, which claims the benefit of Provisional Application No. 60/314,650, filed Aug. 27, 2001, the entire contents of such applications and patents being incorporated by reference in this application.

FIELD OF THE INVENTION

This invention relates to an electrosurgical generator, and to an electrosurgical system comprising a generator and an electrosurgical instrument with two or more treatment electrodes. Such systems are commonly used for the cutting and/or coagulation of tissue in surgical intervention, most commonly in "keyhole" or minimally invasive surgery, but also in laparoscopic or "open" surgery.

BACKGROUND OF THE INVENTION

It is known to provide electrosurgical generators which provide different radio frequency signals for cutting and coagulation, and also to provide a blended signal in which the generator rapidly alternates between the signals for cutting and coagulation. Our U.S. Pat. No. 6,416,509 and also U.S. Pat. No. 3,885,569 to Judson describe blended signals of this type.

SUMMARY OF THE INVENTION

The present invention provides an improvement to this type of electrosurgical system, in that the cutting and coagulation waveforms are delivered to different electrodes of the electrosurgical instrument. Accordingly, there is provided an electrosurgical system including a generator system for generating radio frequency (RF) power, and an electrosurgical instrument including at least three electrodes, the generator system comprising one or more sources of RF output power, and a controller operable to control the generator system such that it is capable of delivering a first cutting RF waveform to the electrosurgical instrument or a second coagulating RF waveform to the electrosurgical instrument, or a timed interruption where no waveform is applied, and, in a combined mode, to deliver both first and second RF waveforms, the system also including means for feeding the waveform to the three or more electrodes such that, in the combined mode, the cutting RF waveforms is delivered between a first pair of the three or more electrodes, and the coagulating RF waveform is delivered between a second pair of the electrodes. The interrupted duration can be such that it can be present in any part of the RF waveform.

Our pending European patent application EP 02255826.6 describes an electrosurgical system in which the operator can select between a cutting signal and a coagulation signal. When the cutting signal is selected, it is supplied to one pair of electrosurgical electrodes, and when the coagulation signal is selected it is supplied to a different pair of electrosurgical electrodes. The present invention is an improvement to this system, in that it also provides a combined mode of operation, but with the different components of the combined signal being supplied to different sets of electrosurgical electrodes. By extension, it is also possible to provide an interruption to the RF output waveform, where no RF applied to any electrode.

The "combined mode" of the generator can be provided in different ways. In one arrangement, the generator system comprises a single source of radio frequency power, and, in the combined mode, the controller is operable to cause the generator system to alternate constantly between delivering the first cutting RF waveform and the second coagulating RF waveform. This is the more traditional "blended" signal of U.S. Pat. Nos. 6,416,509 and 3,885,569. Alternatively, the generator system comprises at least first and second sources of radio frequency power, operating at different frequencies, the first source of radio frequency power being adapted to deliver the first cutting RF waveform, and the second source of radio frequency power being adapted to deliver the second coagulating RF waveform, and, in the combined mode, the controller is operable to cause the generator system to deliver both the first and second RF waveforms simultaneously. This is a different arrangement in which the output of two RF sources is supplied to the instrument simultaneously. Both arrangements have the effect, however, of supplying both cutting and coagulating RF signals to the electrosurgical instrument while the instrument is in use.

Where the alternating blended signal is employed, the means for connecting the waveform conveniently comprises a switching circuit for varying the connections between the source and the three or more electrodes such that, in the combined mode, a first part of the combined signal that is the cutting RF waveform is delivered between a first pair of the three or more electrodes, and a second part of the combined signal that is the coagulating RF waveform is delivered between a second pair of the three or more electrodes.

In a convenient arrangement, the switching circuit of the generator is such that, in the combined mode, the connections between the power supply and the electrodes are switched such that the first part of the blend signal is delivered between the first and second electrodes, and the second part of the blend signal is delivered between the second and third electrodes. In this arrangement, there is a common electrode which is used in both the cutting and coagulation operations, but it is equally feasible to have completely different pairs of electrodes for each function.

Preferably, the switching circuit comprises first and second input connections, first second and third output connections, and an electronic switch connected between the first and second output connections, and being adapted to open and close in order to connect the first and second output connections periodically one to the other. The electronic switch conveniently opens and closes at a frequency of between 5 and 100 Hz. In this arrangement, the second and third output connections are preferably connected one to the other via a capacitor, typically one having a value of between 1 and 10 nF. The switching circuit is conveniently housed in the electrosurgical instrument, although it can alternatively be housed in the electrosurgical generator.

Conveniently, the controller within the generator is adapted to determine The timing of the changes between the first and second parts of the combined signal, or the timing periods associated with an interruption where no RF is applied, and the switching circuit is synchronised to operate in response thereto, so as to deliver the first and second parts of the combined signal respectively to the first and second pairs of electrodes. Alternatively, the switching circuit is adapted to determine the timing of the changes between the first and second parts of the combined signal, and the controller is adapted to operate in response thereto.

Where the combined signal is provided by first and second RF sources acting simultaneously, means for connecting the waveform conveniently comprises one or more output stages arranged such that the cutting RF waveform from the first RF source is delivered between a first pair of the three or more electrodes, and the coagulating waveform from the second RF source is delivered between a second pair of the three or more electrodes. In this way the first and second sources are "hard wired" to deliver their respective waveforms to different output connections, and hence to different pairs of electrodes. Thus the need for active switching of the connections using a switching circuit is avoided, but the power requirements needed for the operation of two RF sources may make this construction unsuitable for some arrangements, such as those in which the generator system is housed within the handpiece of the electrosurgical instrument.

The invention further resides in an electrosurgical system including a generator system for generating RF power, and an electrosurgical instrument including at least three electrodes, the generator system comprising at least one RF output stage, means for supplying power to the at least one output stage, and a controller operable to limit the radio frequency output voltage developed by the at least one output stage to at least a first predetermined threshold value for cutting or vaporisation and a second threshold value for coagulation and, in a combined mode, to deliver waveforms limited to both first and second threshold values, the electrosurgical system also including means for coupling the waveform to the three or more electrodes such that, in the combined mode, a waveform limited to the first threshold value for cutting or vaporisation is delivered between a first pair of the three or more electrodes, and a waveform limited to the second threshold value for coagulation is delivered between a second pair of the three or more electrodes.

The invention further resides in an electrosurgical generator for supplying RF power to an electrosurgical instrument, the generator comprising at least one RF output stage, three more output connections for the delivery of RF power to the electrosurgical instrument, means for supplying power to the at least one output stage, a controller operable to limit the RF output voltage developed by the at least one output stage to at least a first predetermined threshold value for cutting or vaporisation and a second threshold value for coagulation and, in a combined mode, to deliver waveforms limited to both first and second threshold values, and means for feeding the waveforms to the three or more output connections such that, in the combined mode, the waveform that is limited to the first threshold value for cutting or vaporisation is delivered between a first pair of the three or more output connections, and the waveform that is limited to the second threshold value for coagulation is delivered between a second pair of the three or more output connections.

The invention further resides in an electrosurgical system including a generator for generating RF power, and an electrosurgical instrument including at least two electrodes, the generator comprising a RF output stage having two or more output connections, each in electrical connection with a respective one of the at least two electrodes, a power supply coupled to the output stage for supplying power to the output stage, a controller operable to limit the RF output voltage developed across the output connections to at least a first predetermined threshold value for cutting or vaporisation and a second threshold value for coagulation and, in a blend mode, to alternate constantly between the first and second threshold values, and adjustment means, operable by a user of the electrosurgical system, for varying the ratio of the blend mode so as to vary the part of the blend signal that is limited to the first threshold value for cutting or vaporisation, as compared with the part of the blend signal that is limited to the second threshold value for coagulation.

The electrosurgical system of U.S. Pat. No. 6,416,509 is such that the frequency of the blended signal can be pre-set to match the type of electrode intended for use. There is nothing in U.S. Pat. No. 6,416,509 to suggest that the blend ratio (i.e. the ratio of that part of the blended signal that is a cutting or vaporisation signal, as compared with that part which is a coagulation signal) can be pre-set, let alone easily adjusted by the user of the system. Preferably the adjustment means is carried by the electrosurgical instrument, but the adjustment means can also conceivably be mounted on the generator.

The invention will be further described below, by way of example only, with reference to the accompanying drawings.

BRIEF DESCRIPTION OF THE DRAWINGS

FIG. 9 is a block diagram of an alternative embodiment of generator system in accordance with the present invention.

DETAILED DESCRIPTION OF THE PREFERRED EMBODIMENTS OF THE INVENTION

Figure 1:
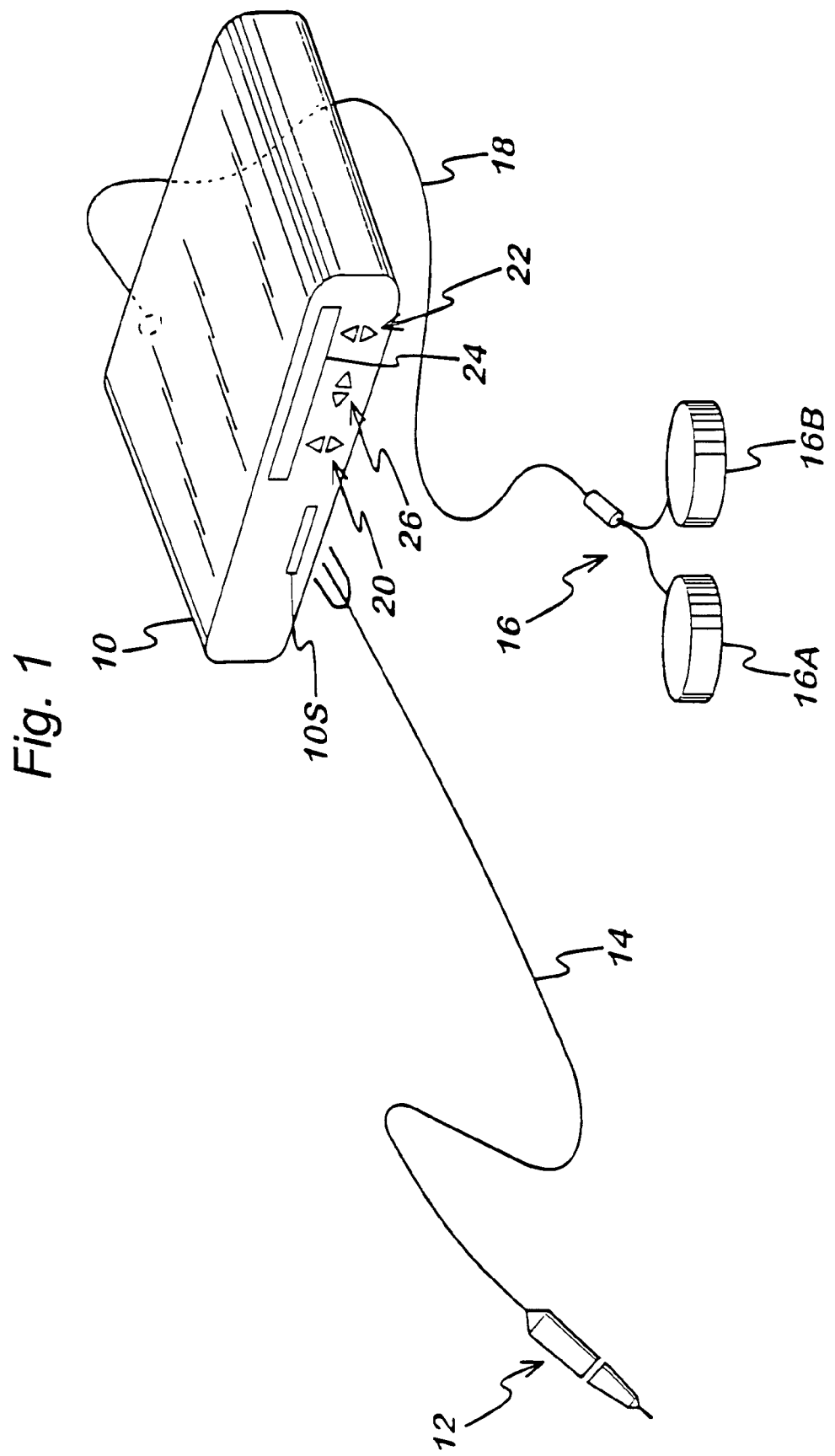
FIG. 1 is a schematic diagram of an electrosurgical system in accordance with the present invention.

Referring to FIG. 1, a generator 10 has an output socket 10S providing a radio frequency (RF) output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two footswitches 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
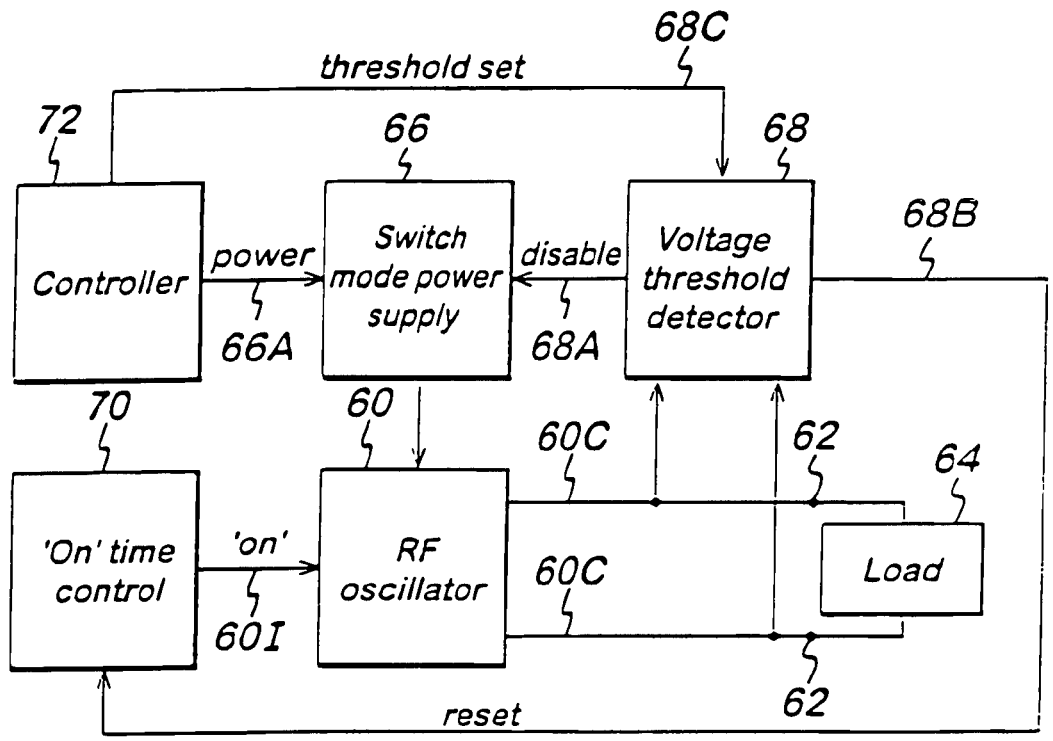
FIG. 2 is a block diagram of the generator of FIG. 1.

Referring to FIG. 2, the generator comprises a radio frequency (RF) power oscillator 60 having a pair of output lines 60C for coupling to the instrument 12. The instrument 12 is shown in FIG. 2 in the form of an electrical load 64. Power is supplied to the oscillator 60 by a switched mode power supply 66. In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output lines 60C is a voltage threshold detector 68 having a first output 68A coupled to the switched mode power supply 16 and a second output 68B coupled to an "on" time control circuit 70. A microprocessor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). A constant output voltage threshold is set independently on the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved. When a combined mode output is required, the voltage output set via input 68C is constantly alternated between the value for desiccation or coagulation and the value for cutting or vaporisation, to form a blended signal.

When the generator is first activated, the status of the control input 601 of the RF oscillator 60 (which is connected to the "on" time control circuit 70) is "on", such that the power switching device which forms the oscillating element of the oscillator 60 is switched on for a maximum conduction period during each oscillation cycle. The power delivered to the load 64 depends partly on the supply voltage applied to the RF oscillator 60 from the switched mode power supply 66 and partly on the load impedance 64. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in our European Patent Application No. 0754437, the disclosure of which is hereby incorporated by way of reference.

Figure 3:
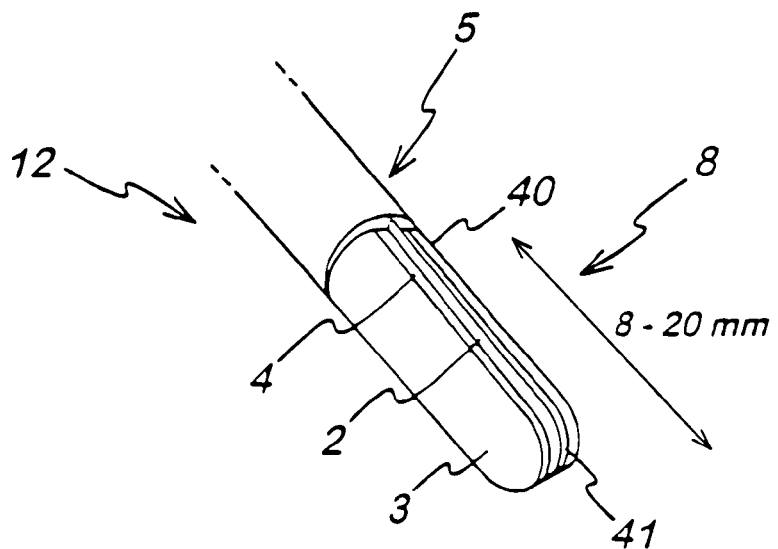
FIG. 3 is a schematic perspective view of an electrosurgical instrument used as a part of the system of FIG. 1.

FIG. 3 shows one possible design for the electrosurgical instrument 12. The instrument 12 comprises an instrument shaft 5 at the distal end of which is an electrode assembly shown generally at 8. The electrode assembly 8 comprises a central cutting electrode 2 disposed between two larger coagulation electrodes 3 and 40. Insulating layer 4 separates the cutting electrode 2 from the first coagulating electrode 3, while an insulating layer 41 separates the cutting electrode 2 from the second coagulation electrode 40. The cutting electrode 2 protrudes slightly beyond the two coagulating electrodes.

When the user intends the instrument to cut tissue, the generator applies a cutting RF signal between the cutting electrode 2 and one or both of the two coagulating electrodes 3 and 40. Conversely, when the user intends the instrument to coagulate tissue, the generator applies a coagulating RF signal between the two coagulating electrodes 3 and 40. The application of the blended RF signal will be described with reference to the switching circuit shown in FIG. 4.

Figure 4:
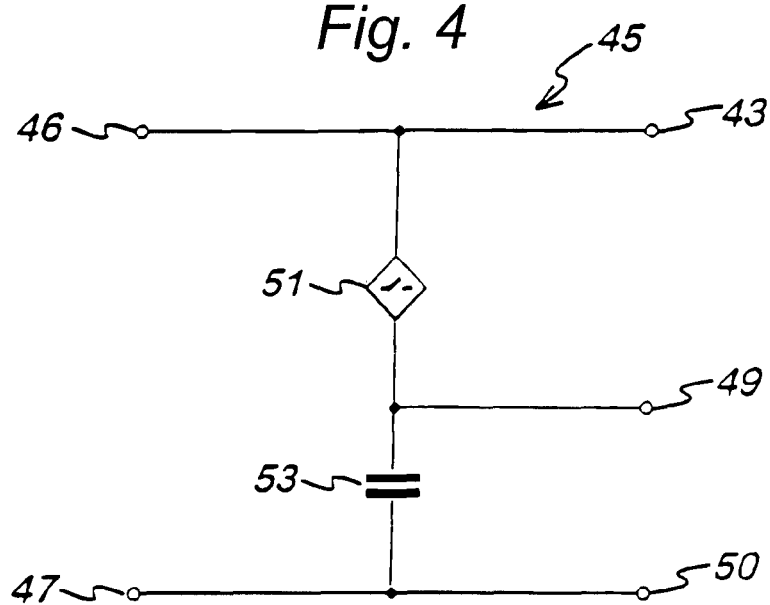
FIG. 4 is a schematic diagram of a switching circuit used in the system of FIG. 1, FIGS. 5A and 5B are circuit diagrams of two electronic switching devices for the switching circuit of FIG. 4.

FIG. 4 shows a switching circuit shown generally at 45 and comprising input connections 46 and 47 connected respectively to the two output lines 60C of the generator 10. Switching circuit 45 has three output connections 48, 49 and 50. Output connection 48 is connected to the cutting electrode 2 in the device of FIG. 3. Output connections 49 and 50 are respectively connected to the coagulating electrodes 3 and 40 in the device of FIG. 3. An electronic switch device 51 is connected between output connections 48 and 49. The switch 51 is capable of rapidly making and breaking the connection between the output lines 48 and 49. A capacitor 53 is connected between the output connections 49 and 50, the capacitor typically having a value of between 1 and 10 nF.

When the user actuates the footswitches 16A or 16B to operate the instrument 12 in the blended mode, the generator supplies alternating bursts of the RF cutting and coagulating signals to the input connections 46 and 47. The switch device 51 operates synchronised with the alternating RF signals such that when that part of the signal containing the cutting signal is received, the switch device is open such that there is open circuit between the output connections 48 and 49. Thus the cutting RF signal is supplied between cutting electrode 2 and coagulating electrode 40, via output connections 48 and 50 respectively. Conversely, when that part of the signal containing the coagulating voltage is received across the input connections 46 and 47, the switching device 51 is closed such that output connections 48 and 49 are in electrical communication one with the other. Thus, during the coagulation part of the blended signal, the signal is supplied between the two coagulation electrodes 3 and 40, via output connections 49 and 50, with the capacitor 53 providing a potential difference there between.

Figure 5A:
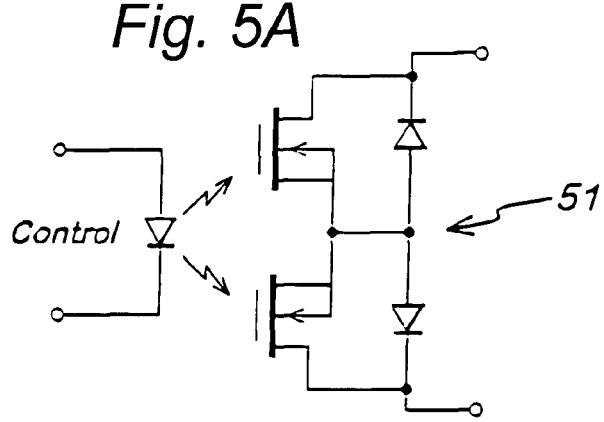

Switching device 51 may comprise an AC opto-relay such as the optically coupled dual FET arrangement shown in FIG. 5A. Another switching device providing isolation between control circuitry and the output lines is the combination of an AC bridge and a single MOSFET switch controlled via an isolating driver, a shown in FIG. 5B.

The above description is based upon the generator 10 controlling the blended mode signal, and the switching device 51 opening and closing synchronously therewith. However, this does not have to be the case and the switching device can control the generator in order to determine the changeover between the cutting and coagulation RF signals.

Consider the switching circuit 45 as shown in FIG. 4. When the switching device 51 is in its open condition, the cutting signal is supplied across output connections 48 and 50. When the switching device 51 closes, the cutting signal is initially supplied between the output connections 49 and 50, separated by the capacitor 53. This causes the current delivered by the generator to rise rapidly such that the current limiting circuitry within the generator operates to reduce the power being delivered, such that the signal rapidly converts to an RF signal typical for coagulation. The effect of the current limiting circuitry within the generator is that the closing of the switching device 51 causes the signal being delivered to be transformed, almost instantaneously, from a cutting signal to a coagulating signal. Conversely, when the switching device 51 opens again, the generator ceases to be current limited, and the signal once again rapidly reverts to being a cutting RF signal. In this way, the opening and closing of the switching device 51 toggles the generator between its cutting and coagulating modes, producing the blended signal which is supplied to the electrodes of the instrument 12.

Figure 6:
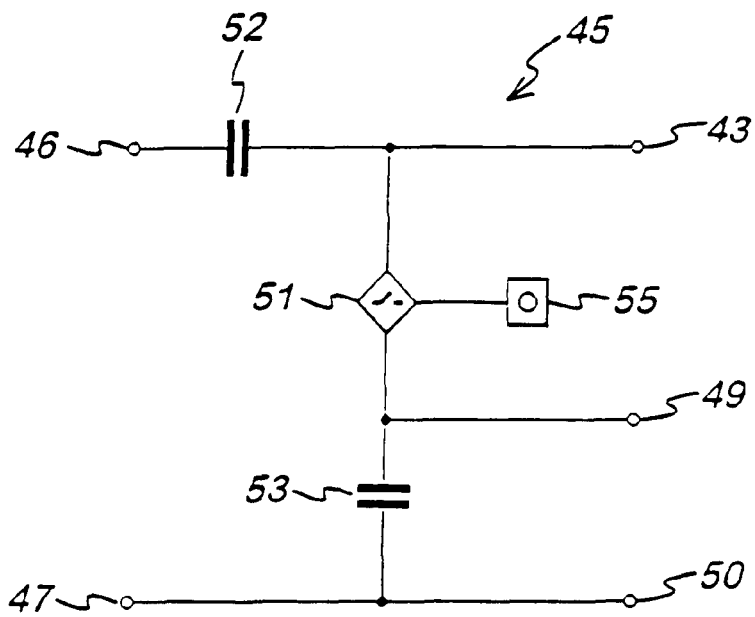
FIG. 6 is a schematic diagram of an alternative embodiment of switching circuit which can be used in the system of FIG. 1.

FIG. 6 shows an alternative embodiment of switching circuit, which can be employed if the generator 10 is not a current limited generator, or if it is desired not to use the current limiting features of the generator. The switching circuit of FIG. 6 is almost identical to that of FIG. 4, the main difference being the addition of an additional capacitor 52 in series with the input connection 46. The capacitor 52 typically has a value one half of that of capacitor 53, such that the voltage delivered across output connections 49 and 50 is divided down to a level typically used for coagulation without reducing the power output of the generator 10. In this way a cutting RF signal is delivered between output connections 48 and 50 when the switching device 51 is open, and a coagulating RF signal is delivered between output connections 49 and 50 when the switching device is closed.

Figure 7:
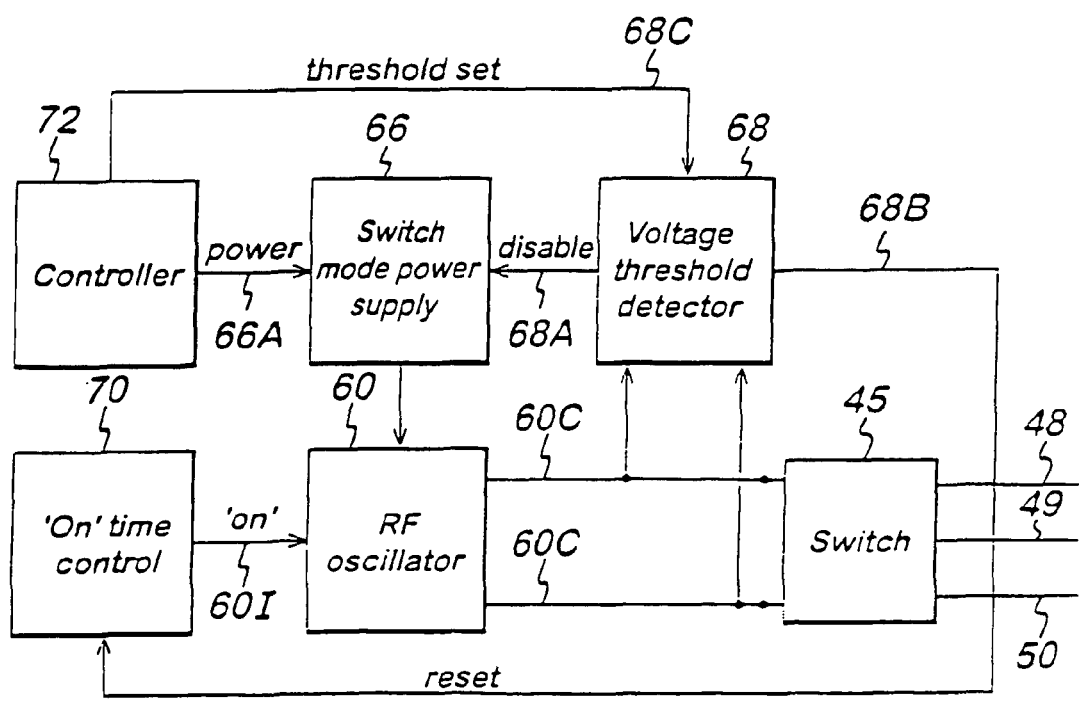
FIG. 7 is a block diagram of a generator in accordance with FIG. 2, incorporating a switching circuit in accordance with FIG. 4, FIGS. 8A to 8C are diagrams illustrating techniques for adjusting a blend switching ratio, FIGS. 8A and 8C being circuit diagrams of alternative ratio adjusting devices and FIG. 8B being a waveform diagram illustrating the operation of the device of FIG. 8A.

Switching circuit 45 can be provided within the electrosurgical instrument 12, or within the output stage of the generator 10 as shown in FIG. 7. Wherever the switching circuit 45 is located, the switching device can be provided with an adjustment device 55, (as shown in FIG. 6) operable by the user of the system in order to adjust the timing of the switching device. By operating the adjustment device 55, the user is able to alter the ratio between that part of the blended RF signal which is a cutting signal, and that part which is a coagulating signal. Whether the adjustment device 55 is located on the instrument 12 or the generator 10, the user of the system can vary the signal so as to increase or decrease the coagulating component of the blended signal with respect to the cutting component, and vice versa. This gives considerable flexibility to the electrosurgical system in terms of its use as a simultaneous cutting and coagulation device, with user-operable control of how much coagulation is provided.

Figure 5B:
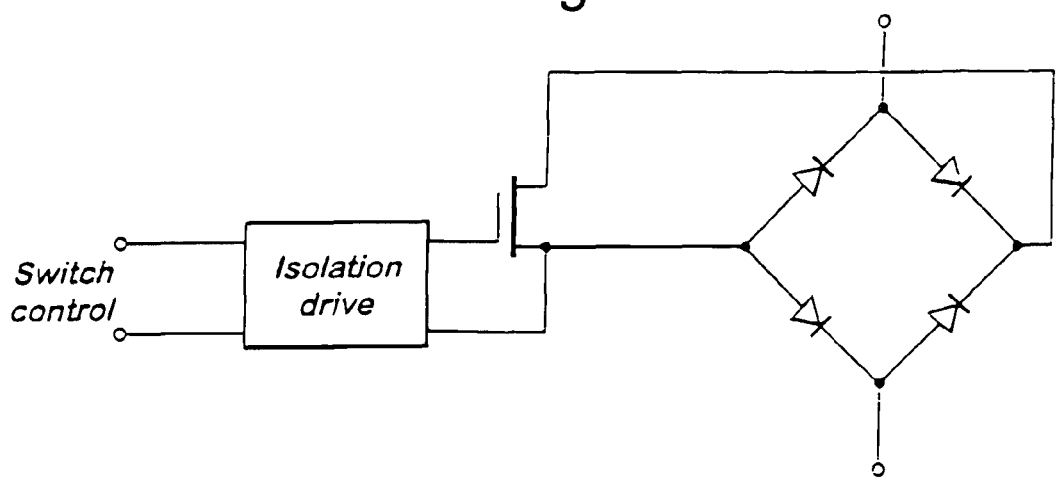

As in the arrangement described above in FIG. 4, the switching device 51 of the alternative switching circuit of FIG. 6 may be as shown in FIG. 5A or FIG. 5B, the driving signal being obtained from a source associated with the switching device itself or from control circuitry within the generator which controls other generator functions.

Figure 8A:
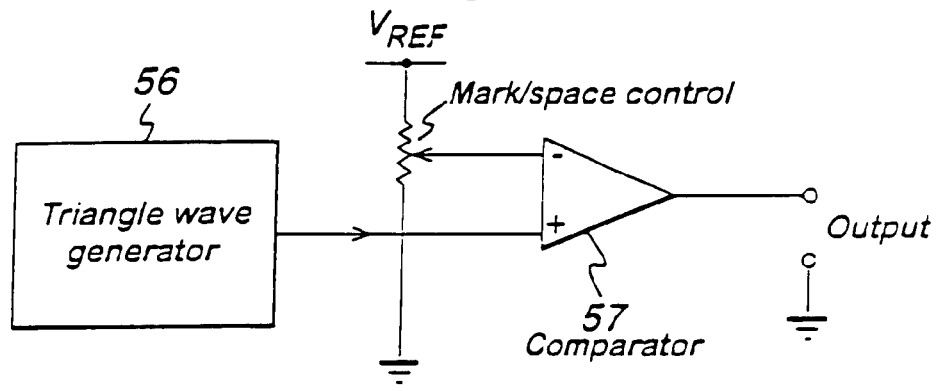
Figure 8B:
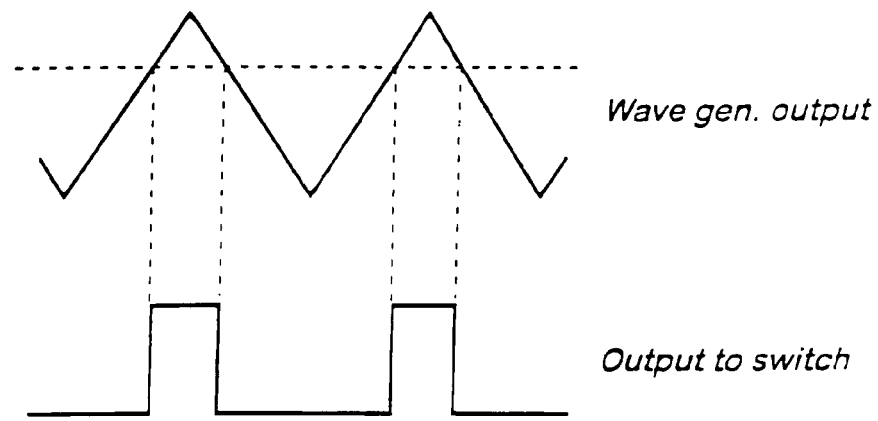
Figure 8C:
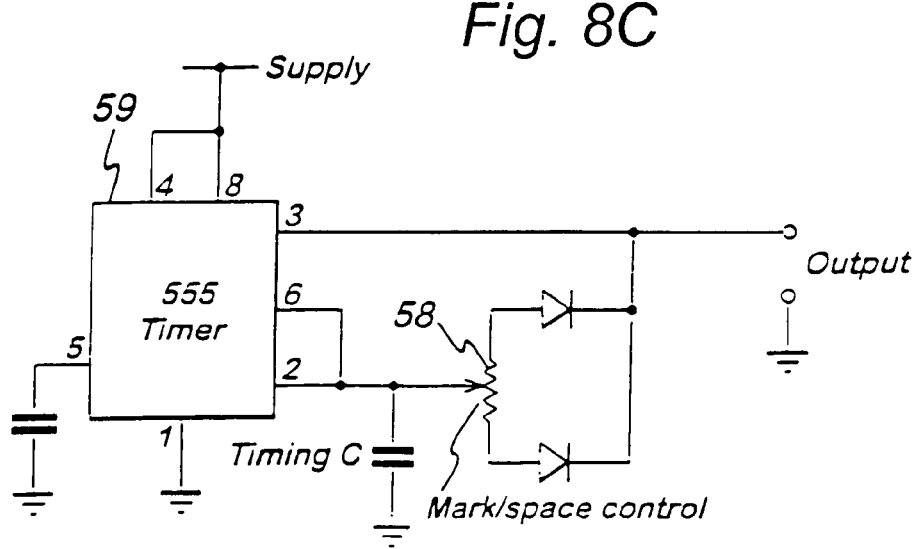

Various circuits for implementing the adjustment device 55 will be apparent to those skilled in the art. An example of a circuit in which a blended mode signal is generated by elements associated with the switching device and has a variable mark-to-space ratio is shown in FIG. 8A. In this case, the output of a triangular wave generator 56 is compared in a comparator 57 with a user-adjustable reference voltage to produce a square wave of the switching device 51 (FIG. 6). Another circuit generating an adjustable blended mode switching device control signal is shown in FIG. 8C. Here, a user-operable potentiometer 58 is coupled with a timer circuit 59 using a 555 i.c.

FIG. 9 shows an alternative generator system in which two RF source circuits 74 and 74' are employed. Source circuit 74 comprises RF oscillator 60 and its associated power supply and control elements. The source circuit is as described with reference to FIG. 2, and like elements are given the same reference numerals as in FIG. 2. The second source circuit 74' comprises a second RF oscillator 60', along with a second controller 72', power supply 66', voltage threshold detector 68' and on time control circuit 70'. FIG. 9 shows the source circuit 74' as having its own dedicated version of each of these units, although it is feasible that certain of them (such as the power supply 66' and controller 72') could be shared with the source circuit 74. The voltage threshold detector 68 is set such that the output connections 60C from source circuit 74 provide an output power signal having a cutting RF waveform, while the voltage threshold detector 68' is set such that the output connections 60C' from source circuit 74' provide an output power signal having a coagulating RF waveform. The second oscillator 60' operates at a different frequency from that of oscillator 60.

A common output stage 73 is provided for both source circuits 74 and 74'. Output connections 60C from source circuit 74 are connected to input connections 46 and 47 of the output stage 73, while output connections 60C' from source circuit 74' are connected to input connections 46' and 47' of the output stage respectively. Within the output stage 73, input connections 47 and 47' are both connected to output connection 49, while input connection 46 is connected to output connection 48, and input connection 46' to output connection 50. The result of this arrangement is that the cutting RF signal from source circuit 74 is delivered between output connections 48 and 49 and hence to one pair of electrodes on the electrosurgical instrument 12. Simultaneously, the coagulating RF signal from source circuit 74' is delivered between output connections 49 and 50 and hence to a different pair of electrodes of the instrument 12. Thus the electrosurgical instrument 12 is able simultaneously to cut and coagulate tissue by virtue of the two different frequency signals. As before, the advantage is that the cutting signal and the coagulating signal, whether they be applied simultaneously or in an alternating blended signal, are delivered to different pairs of electrodes of the electrosurgical instrument. The design of these electrodes can therefore be optimised, depending on whether they are intended to cut or coagulate tissue.

Figure 10:
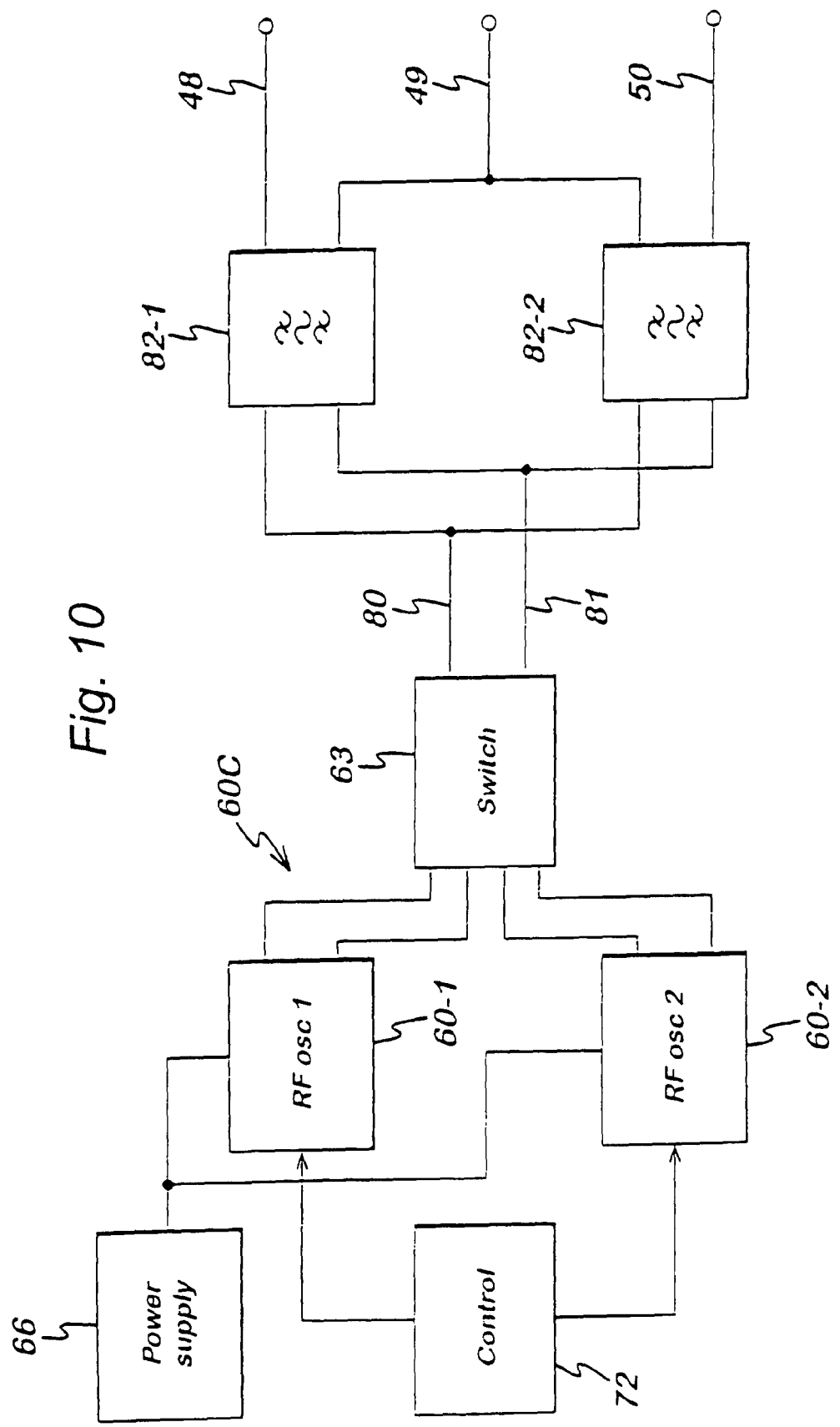
FIG. 10 is a block diagram of a further alternative system in accordance with the invention.

Referring to FIG. 10, in an further alternative generator and instrument combination, two RF power oscillators 60-1 and 60-2 are powered from a common power supply 62 and are controlled by a common controller 72 to produce on respective output lines 60C an RF power signal suitable for cutting and an RF power signal suitable for coagulation. These signals may be fed to a switching circuit 63 for selecting the power signal from one oscillator 60-1 or the other oscillator 60-2 according to inputs from, for instance, foot switches, the selected power signal being transmitted on output connections 80, 81. In a blended mode, the switch is operated repeatedly at a predetermined rate to produce a blended output power signal across connections 80, 81. The power oscillators 60-1, 60-2 are operated at different frequencies, and the respective cut and coagulation signals are fed to the required electrodes by feeding the power signal on output connections 80, 81 to tuned circuits 82-1 and 82-2 tuned to the different frequencies. The outputs of the tuned circuits are coupled via electrode lines 48, 49 and 50 to the respective electrodes of the electrosurgical instrument. In this way, the cutting signal from oscillator 60-1 is fed to a cutting electrode 48 and a common electrode 49, whereas the coagulation signal from oscillator 60-2 is fed to a coagulation electrode 50 and the common electrode 49.

In the embodiment shown in FIG. 10, the connection between the electrosurgical generator and the electrosurgical instrument is typically provided by output connections 80 and 81, but the apportionment of circuit blocks between the generator and the instrument may be varied.

Figure 11A:
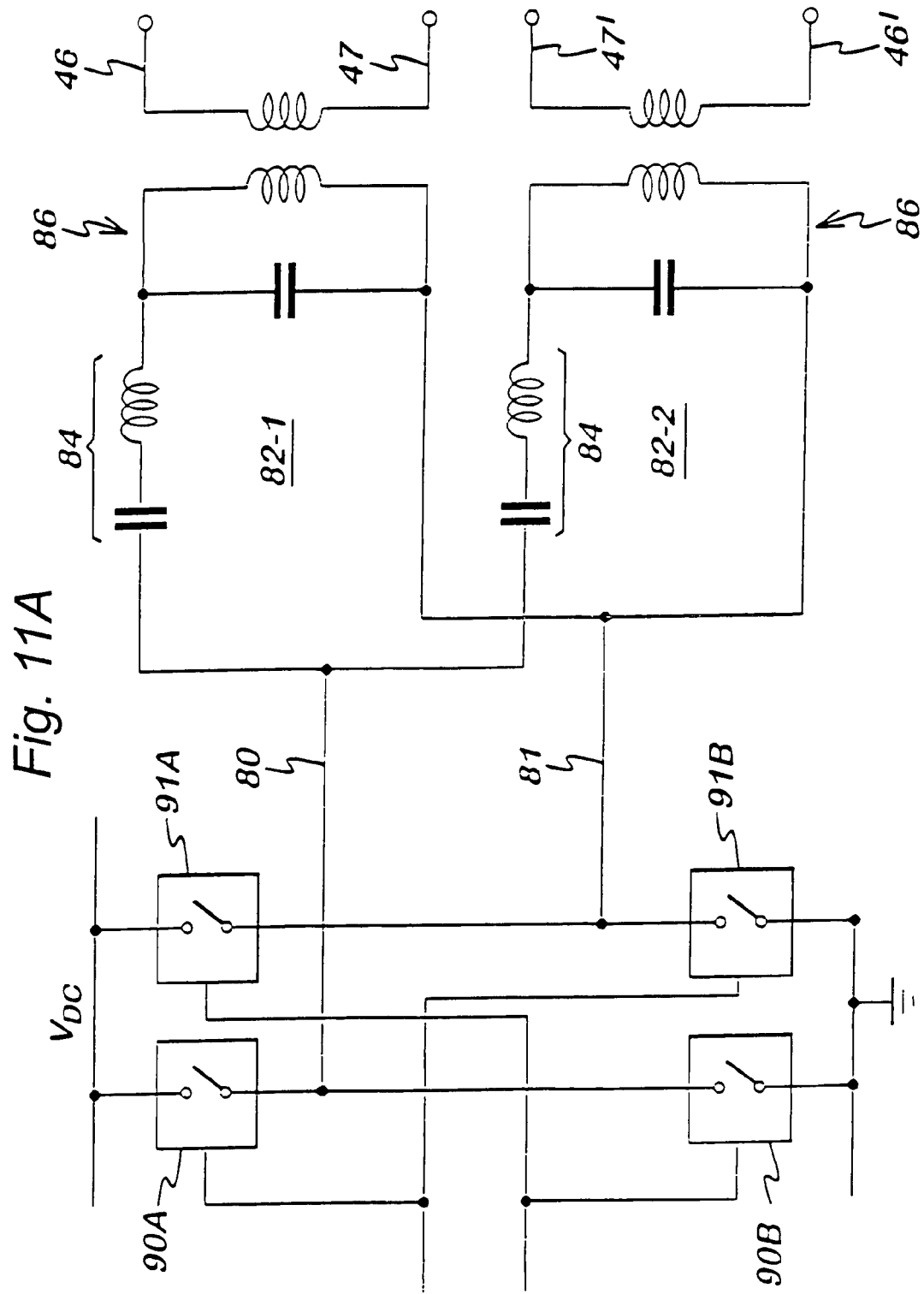
FIGS. 11A and 11B are yet further alternative systems for feeding cut and coagulation outputs automatically to different respective electrode pairs.
Figure 11B:
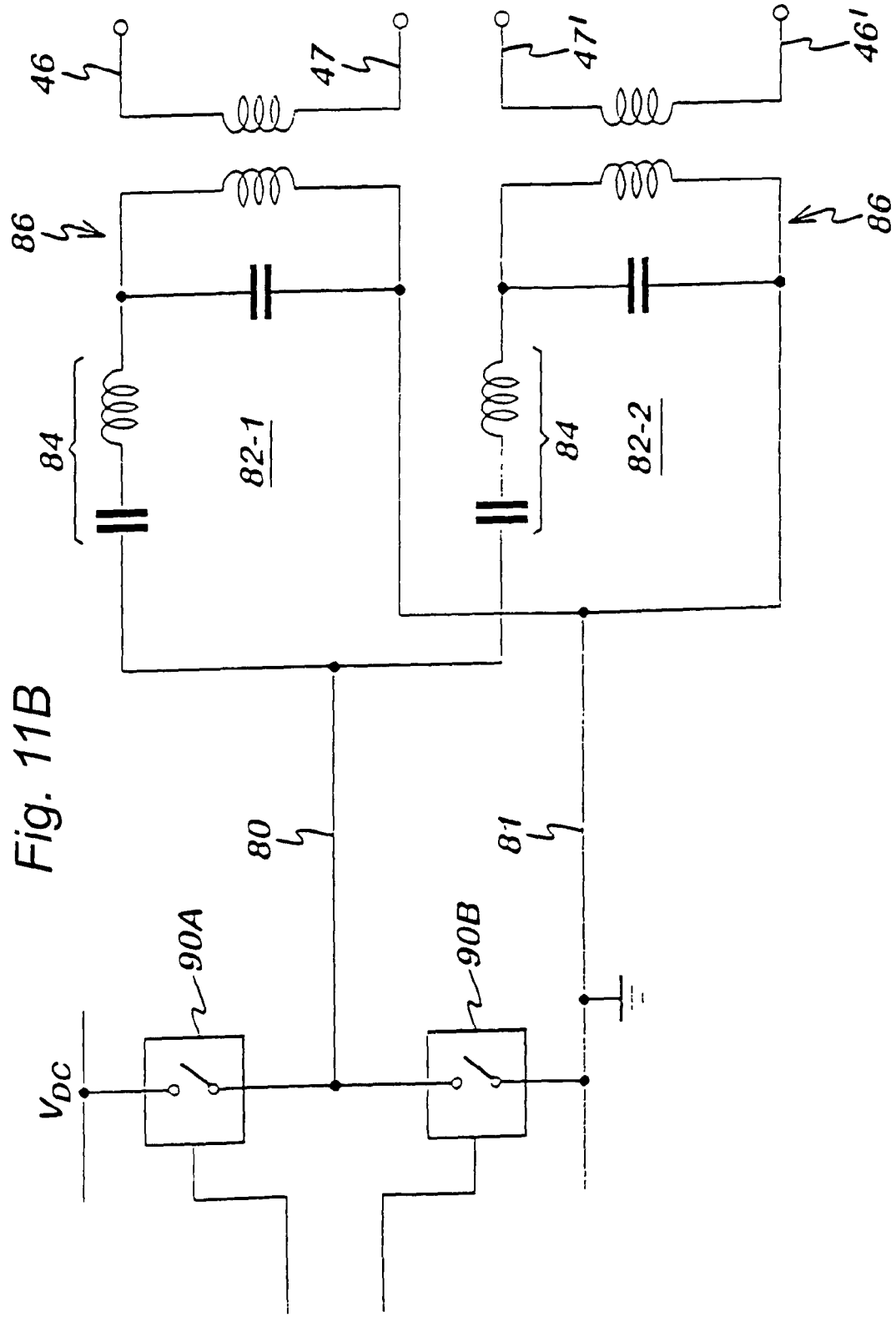

Further embodiments are shown in FIGS. 11A and 11B. Like the embodiment of FIG. 9, these embodiments dispense with the need for a signal routing switch or switching circuit.

Referring to FIG. 11, there are provided two tuned circuits 82-1 and 82-2 (as in FIG. 10), tuned to different frequencies. Each has a series-resonant inductor-capacitor pair 84 and a parallel-resonant inductor-capacitor pair 86, the latter being transformer coupled to output connections 46 and 47 on the one hand and 46' and 47' on the other hand. As in the embodiment of FIG. 10, each tuned circuit has two inputs, one of which is connected to a generator output connection 80 and the other of which is connected to a generator output connection 81. In this embodiment, the generator has an output stage comprising RF switches arranged in two oppositely acting push-pull pairs 90A, 90B and 91A, 91B. Typically these switches comprise power MOSFETS. Each switch 90A, 90B, 91A, 91B is connected to driver inputs 92, 93, as shown, which receive an RF drive signal which, for producing on the output connections 80, 81 an output having a cut waveform is at one RF frequency, and for producing a coagulation output on the output connections 80, 81, has a different RF frequency, these frequencies being, respectively, the resonant frequency of, the resonant combinations 84, 86 of the first tuned circuit 82-1 and, the resonant frequency of the corresponding resonant combinations of the other tuned circuit 82-2. As described above, the RF switches 90A, 90B, 91A and 91B of the generator output stage may be driven according to, for instance, a footswitch control to produce a cut output or a coagulation output. Again, additionally, a blended output may be produced in which the RF frequency alternates constantly between the two resonant frequencies of the tuned output circuits.

The embodiment of FIG. 11B is a modification of that of FIG. 11A, in which the generator output stage has a single push-pull pair of RF switches 90A, 90B and in which the tuned circuits each have one input connected to the junction between the switches 90A, 90B and the other input connected to ground.

Referring again to FIG. 2, this figure shows an "'on' time control" circuit 70 for providing a timing control signal 60I to RF oscillator 60. Signal 60I provides a defined period when the RF oscillator 60 is enabled to oscillate and provide an RF waveform to load 64. By having a timed processing element present in the "on-time control" circuit 70, the RF oscillator 60 can be inhibited so as to produce an interruption in the applied RF waveform so that the oscillator provides no RF waveform to load 64.

FIG. 7 shows a circuit arrangement similar to that shown FIG. 2. However, FIG. 7 also includes a switch 45, which shows that the switching of the RF waveform output to the output electrode connections 48, 49 and 50 is separate from the "'on' control signal" 60I. The RF waveform on/off switching control can therefore be operated independently from the output electrode connection switching.

This design of separating the output selection from internal control signals is disclosed elsewhere in the present application. For example, the output voltage control (i.e., cut voltage or coag voltage) is provided by means of the 'threshold set' signal applied from the controller 72 to the Voltage threshold detector 68. This is independent and separate from the output switch 45.

The interruption control is therefore achieved by the RF oscillator control. Since the RF oscillator is not providing any RF power, then the state of the switching device 51 used to route the RF output waveform is not important.

FIG. 9 shows how the controller 72 could inhibit both RF sources 60-1 and 60-2 so that no RF power is applied to switch 73. This would result in no RF power being available and would correspond to the interruptions shown in FIGS. 12B to 12D between the cut and coag output waveforms 100 and 102 shown in such figures. FIG. 10 is an alternative to the system described in FIG. 9. Controller 72 can be seen providing and input signal into RF OSC1 (60-1) and RF OSC2 (60-2), this being remote from the switch 63.

Figure 12A:
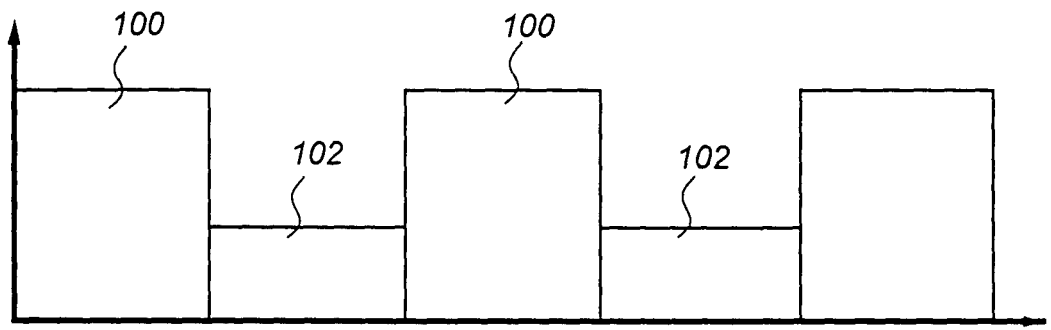
FIGS. 12A to 12D show various relationships between cut and coag signals and interruptions between such signals.
Figure 12B:
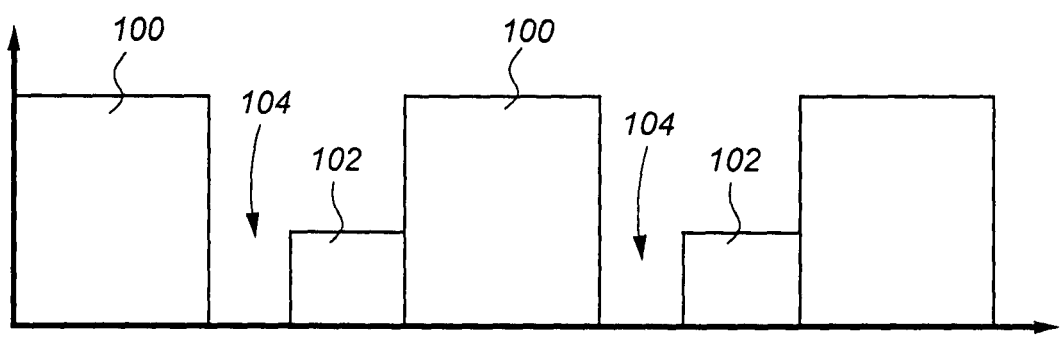
Figure 12C:
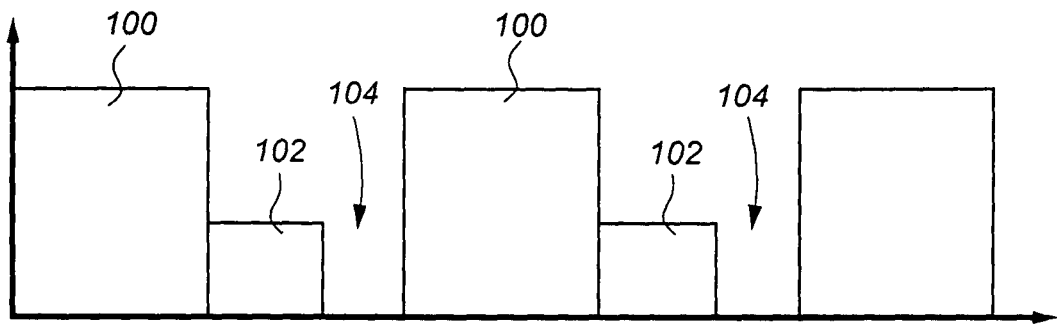
Figure 12D:
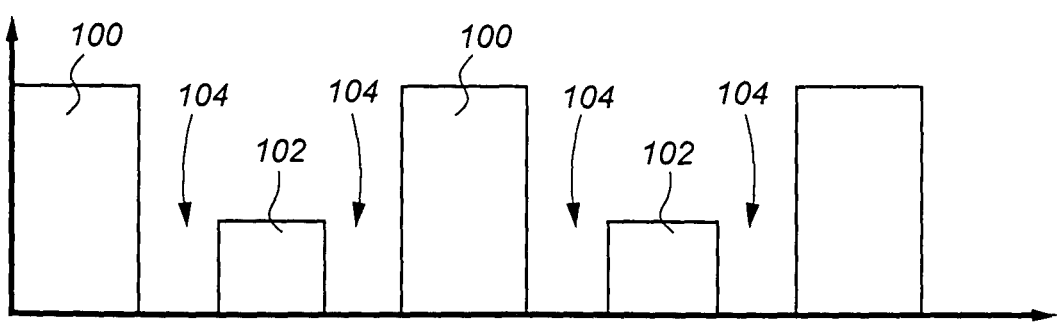

The waveforms shown in FIG. 12A show the relationship between cut and coag waveforms 100 and 102, respectively, and the lack of a period of interruption between such waveforms in a standard blend mode of operation. However, as can be seen in FIGS. 12B to 12D, the proportion and location of a period of interruption 104 to cut and coag waveforms 100 and 102 can vary, depending on the required blend function for the particular tissue to be treated and/or the surgical procedure to be performed. For non-simultaneous implementations of the blend function, the cut and coag waveforms 100 and 102 alternate in a timed manner without interruption, as shown in FIG. 12A, where the taller waveform 100 is the cut waveform and the lower waveform 103 is the coag waveform. The interruption period 104 can occur in a number of positions in the with respect to the blend function waveforms. For example, the interruption period 104 can be applied after the cut voltage waveform 100 is output and before the subsequent coag voltage waveform 102 is output, as shown in FIG. 12B. The interruption period 104 can also occur after the coag voltage waveform 102 is output and before the subsequent cut voltage waveform 100 is output, as shown in FIG. 12C. The interruption period 104 can further occur after both the coag voltage waveform 102 is output and before the subsequent cut voltage waveform 100 is output, as shown in FIG. 12D. As can be seen in FIGS. 12B to 12D, the occurrence of the interruption period 104 is shown as reducing the time duration of the coag voltage waveform 102. However, it should be noted that the occurrence of the interruption period 104 can alternatively reduce the time duration of the cut voltage waveform 100.

The waveforms shown in FIGS. 12A to 12D all have the same cut voltages and coag voltages used. It is clearly possible to apply a whole range of modifications to the cut and coag voltages to further enhance the flexibility and capability of the blend function. These include, and are not limited to, changes to the individual cut and coag voltage with respect to time and the relationship of the cut and coag voltages themselves.

The period of the interruption can also be changed in response to a sensed clinical parameter, such as, for example, tissue impedance. This would have the effect of also reducing the applied power.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:
1. An electrosurgical system comprising:
a generator system for generating radio frequency (RF) power, and
an electrosurgical instrument including an instrument shaft, at the distal end of which is an electrode assembly including three or more electrodes, the generator system comprising:
(i) one or more sources of RF output power, and
(ii) a controller operable to control the generator system such that it is capable of delivering a first cutting RF waveform to the electrosurgical instrument or a second coagulating RF waveform to the electrosurgical instrument, and, in a combined mode, to deliver a combination of both first and second RF waveforms,
the electrosurgical system further comprising means for feeding the RF waveforms to the three or more electrodes such that, in the combined mode, the cutting RF waveform is delivered between a first pair of the three or more electrodes, and the coagulating RF waveform is delivered between a second pair of the three or more electrodes, and the controller is operable to cause the feeding means to switch between delivering the first cutting RF waveform between the first pair of electrodes and delivering the second coagulating RF waveform between the second pair of electrodes.

2. An electrosurgical system according to claim 1 wherein the feeding means is adapted to supply the first cutting RF waveform and the second coagulating RF waveform discontinuously so that there are interruptions between the feeding of the RF waveforms.

3. An electrosurgical system according to claim 2 wherein the feeding means is adapted to supply the first cutting RF waveform and the second coagulating RF waveform so that there are interruptions between the delivery of the first cutting RF waveform and the second coagulating RF waveform.

4. An electrosurgical system according to claim 2 wherein the feeding means is adapted to supply the first cutting RF waveform and the second coagulating RF waveform so that there are interruptions between the delivery of the second coagulating RF waveform and the first cutting RF waveform.

5. An electrosurgical system according to claim 2 wherein an interruption period occurs after the cutting RF waveform is output and before the coagulating RF waveform is output.

6. An electrosurgical system according to claim 2 wherein an interruption period occurs after the coagulating RF waveform is output and before the cutting RF waveform is output.

7. An electrosurgical system according to claim 2 wherein an interruption period occurs after both the coagulating RF waveform is output and before the cutting RF waveform is output.

8. An electrosurgical system according to claim 2 wherein the interruptions between the delivery of the RF waveforms results in a reducing of the time duration of the coagulating RF waveform.

9. An electrosurgical system according to claim 2 wherein the interruptions between the delivery of the RF waveforms results in a reducing of the time duration of the cutting RF waveform.

10. An electrosurgical system according to claim 2, wherein the means for feeding the waveforms comprises a selection arrangement for discontinuously varying the coupling between the source and the three or more electrodes such that, in the combined mode, a first part of the combined signal that is the cutting RF waveform is delivered between a first pair of the three or more electrodes, and a second part of the combined signal that is the coagulating RF waveform is delivered between a second pair of the three or more electrodes.

11. An electrosurgical system according to claim 10, wherein the selection arrangement is a switching circuit comprising first and second input connections, first second and third output connections, and an electronic switch connected between the first and second output connections, and being adapted to open and close in order to connect the first and second output connections periodically one to the other.

12. An electrosurgical system according to claim 11, wherein the electronic switch opens and closes at a frequency of between 5 and 100 Hz.

13. An electrosurgical system according to claim 11, wherein the second and third output connections are connected one to the other via a capacitor.

14. An electrosurgical system according to claim 13, wherein the capacitor has a value of between 1 and 10 nF.

15. An electrosurgical system according to claim 2, wherein the feeding means is housed within the electrosurgical instrument.

16. An electrosurgical system according to claim 2, wherein the feeding means is housed within the generator system.

17. An electrosurgical system according to claim 2, wherein the controller is adapted to determine the timing of the interruptions between the first and second waveforms, and the feeding means is synchronised to operate in response thereto.

18. An electrosurgical system according to claim 2, wherein the feeding means is adapted to determine the timing of the interruptions between the first and second waveforms, and the controller is adapted to operate in response thereto.

19. An electrosurgical system according to claim 2, wherein the generator system comprises at least first and second sources of RF power, operating at different frequencies, the first source of RF power being adapted to deliver the first cutting RF waveform, and the second source of RF power being adapted to deliver the second coagulating RF waveform, and, in the combined mode, the controller is operable to cause the generator system to deliver the first and second RF waveforms discontinuously.

20. An electrosurgical system according to claim 19, wherein the first and second sources of RF power have respective pairs of output lines, and wherein the output lines of the first source are connected to a first pair of the three or more electrodes and the output lines of the second source are connected to a second pair of the three or more electrodes.

21. An electrosurgical system according to claim 20, wherein the pairs of output lines have a common line which is connected to one of the three or more electrodes.

22. An electrosurgical system according to claim 19, wherein the means for feeding the waveforms to the electrodes comprise one or more output stages arranged such that the cutting RF waveform from the first RF source is at least mainly delivered between a first pair of the three or more electrodes, and the coagulating waveform from the second RF source is at least mainly delivered between a second pair of the three or more electrodes.

23. An electrosurgical system according to claim 22, wherein the output stages comprise first and second resonant output circuits tuned, respectively, to first and second frequencies and connected respectively to the first and second pairs of electrodes.

24. An electrosurgical system according to claim 1, having an RF power source operable in response to the controller to generate on a common pair of output lines an RF power signal which, in the combined mode, alternates discontinuously between delivering a first cutting RF waveform at a first frequency and delivering a second coagulating RF waveform at a second frequency, wherein the means for feeding the waveform to the electrodes comprises first and second resonant output circuits coupled to said output lines and tuned respectively to the first and second frequencies, the first resonant output circuit being connected to the first pair of electrodes and the second resonant output circuit being connected to the second pair of electrodes.

25. An electrosurgical system according to claim 24, wherein the controller and the RF power source are operable together to limit the peak RF output voltage to a first predetermined threshold when delivering the cutting RF waveform and to a second predetermined threshold when delivering the coagulating RF waveform.

* * * * *